United States Patent
Dehaine et al.

(10) Patent No.: US 12,056,822 B2
(45) Date of Patent: Aug. 6, 2024

(54) DEVICE AND METHOD FOR INTRAOPERATIVE RECONSTRUCTION OF BONE 3D MODELS

(71) Applicant: GANYMED ROBOTICS, Paris (FR)

(72) Inventors: Baptiste Dehaine, Paris (FR); Marion Decrouez, Sèvres (FR); Nicolas Loy Rodas, Gennevilliers (FR)

(73) Assignee: GANYMED ROBOTICS, Paris (FR)

( * ) Notice: Subject to any disclaimer, the term of this patent is extended or adjusted under 35 U.S.C. 154(b) by 0 days.

(21) Appl. No.: 18/410,211

(22) Filed: Jan. 11, 2024

(65) Prior Publication Data
US 2024/0233267 A1   Jul. 11, 2024

(30) Foreign Application Priority Data

Jan. 11, 2023 (EP) ..................................... 23305038

(51) Int. Cl.
| | |
|---|---|
| *G06T 17/20* | (2006.01) |
| *G06T 5/20* | (2006.01) |
| *G06T 5/70* | (2024.01) |
| *G06T 7/33* | (2017.01) |
| *G06T 15/06* | (2011.01) |
| *G16H 50/50* | (2018.01) |

(52) U.S. Cl.
CPC ................ *G06T 17/20* (2013.01); *G06T 5/20* (2013.01); *G06T 5/70* (2024.01); *G06T 7/344* (2017.01); *G06T 15/06* (2013.01); *G16H 50/50* (2018.01); *G06T 2200/04* (2013.01); *G06T 2207/10116* (2013.01); *G06T 2210/41* (2013.01)

(58) Field of Classification Search
None
See application file for complete search history.

(56) References Cited

U.S. PATENT DOCUMENTS

2010/0189320 A1* 7/2010 Dewaele ............... G06T 7/11
382/128

OTHER PUBLICATIONS

B. Aubert, T. Cresson, J. A. de Guise and C. Vazquez, "X-Ray to DRR Images Translation for Efficient Multiple Objects Similarity Measures in Deformable Model 3D/2D Registration," in IEEE Transactions on Medical Imaging, vol. 42, No. 4, pp. 897-909, Apr. 2023, doi: 10.1109/TMI.2022.3218568. (Year: 2023).*

T.Whitmarsh,L. Humbert,M. DeCraene,L. M. DelRioBarquero & A.F. Frangi, "Reconstructing the 3D Shape and Bone Mineral Density Distribution of the Proximal Femur From Dual-Energy X-Ray Absorptiometry," IEEE Transactions on Medical Imaging, vol. 30, No. 12 , pp. 2101-2114, Dec. 2011, doi: 10.1109/TMI.2011.2163074. (Year: 2011).*

Fleut Markus, "Shape Reconstruction for Computer Assisted Surgery based on Non-Rigid Registration of Statistical Models with intraoperative Point Data and X-ray Images," Thesis, dated Oct. 3, 2001, retrieved on Jun. 14, 2023 from https://theses.hal.science/tel-00005365.

(Continued)

*Primary Examiner* — James A Thompson
(74) *Attorney, Agent, or Firm* — Morgan, Lewis & Bockius LLP

(57) ABSTRACT

The present invention relates to a device and a computer implemented method for reconstruction of a 3D model (31) of an exposed target anatomical structure (T) of a patient during surgery.

15 Claims, 5 Drawing Sheets

(56) References Cited

OTHER PUBLICATIONS

Reyneke Cornelius Johannes Frederik, et al., "Review of 2-D/3-D Reconstruction Using Statistical Shape and Intensity Models and X-Ray Image Synthesis: Toward a Unified Framework" IEEE Reviews in Biomedical Engineering, vol. 12, pp. 269-286.
Rusinkiewicz, Szymon et al., "Efficient Variants of the ICP Algorithm," 3-D Digital Imaging and Modeling, 2001. Proceedings. Third International AL. Conference on May 28-Jun. 1, 2001, Piscataway, NJ, IEEE, pp. 145-152.
European Search Report and Written Opinion for related European Patent Application No. EP 23305038, dated Jun. 23, 2023, 10 pages.

* cited by examiner

DEVICE AND METHOD FOR INTRAOPERATIVE RECONSTRUCTION OF BONE 3D MODELS

CROSS-REFERENCE TO RELATED APPLICATIONS

This application claims priority to European Patent Application No. EP 23305038.4, filed Jan. 11, 2023, the entirety of which is incorporated herein by reference.

FIELD OF INVENTION

The present invention relates to the field of medical imaging processing for use during surgery. Notably the invention concerns to a method and a device for the reconstruction of a 3D model of an exposed target anatomical structure of a patient during surgery.

BACKGROUND OF INVENTION

Clinically, obtaining accurate 3D models of the patient's bones is crucial for surgical planning, implant fitting, surgical navigation, robot-assisted surgery, and postoperative evaluation in orthopedics. Nowadays, in most cases, the models are obtained by post-processing 3D medical imaging data such as CT scans and/or MRI.

Conventional X-ray imaging significantly reduces the exposure of patients to ionizing radiation compared to Computer Tomography (CT) imaging and is much more common and inexpensive compared to Magnetic Resonance Imaging (MRI) scanners. However, retrieving 3D models solely from X-ray images is significantly more challenging, and additional processing is required to reconstruct an accurate 3D model from 2D images, in comparison to retrieving 3D models from 3D images from CT or MRI scanner. In order to reduce the associated costs and additional radiation exposure from CT-scan, several solutions combining data extracted from X-rays with Statistical Models of bones have been developed. These approaches also often rely on bone surface data acquired intraoperatively through the digitization of the bone surface and anatomical landmarks using a specific probe (known as "Bone Morphing"). These "Image-less" solutions (i.e., not requiring a preoperative CT-scan) are present today on several surgical navigation products to approximate the 3D shape of bones to operate.

While "Image-less" products are popular, the accuracy of the reconstructed bone model is reduced since X-ray do not provide volumetric and 3D information. Digitization of the bone during surgery brings additional surface shape information, yet, this requires the use of an optical tracking system with markers rigidly fixed to bone. Digitization adds significant time to the surgery since the surgeon must capture data of all the exposed surface of the bone using a probe. This step is tedious to the surgeon and is prone to errors. Indeed, wrong digitizations (e.g., not touching the bone properly) result in noisy data captured during the digitization step. The reconstructed models can present high errors in complex regions of the bone not visible in the X-rays used as input. Also, bony anomalies specific to the patient are hardly reproducible in statistical models.

In this context, there is a need to develop a solution allowing to avoid the use of 3D imaging systems, such as CT or MRI scanner, while sensibly improving the accuracy of reconstruction of 3D model of the target bone, which will reduce errors during the surgery.

SUMMARY

The present invention aims at fulfilling the need to develop such a solution.

To achieve this aim, the invention proposes a device for the reconstruction of a 3D model of an exposed target anatomical structure of a patient during surgery, said device comprising:

at least one input configured to receive:
- at least one 2D X-ray image comprising at least one portion of the target anatomical structure;
- at least one 3D image acquired from at least one 3D imaging sensor during surgery, wherein the at least one 3D image comprises data points representing at least one exposed portion of the target anatomical structure;
- a predefined shape model of the target anatomical structure;

at least one processor configured to compute the 3D model of the exposed target anatomical structure via an iterative method following the steps below:
a) set a candidate 3D shape based on the predefined shape model;
b) compute a 2D digitally reconstructed radiography using a digitally reconstructed radiography processing function characterized by a set of projection parameters on the candidate 3D shape;
c) register a corresponding portion of said candidate 3D shape to at least part of the 3D image data points and compute a similarity transformation between the data points of said candidate 3D shape and corresponding data points of the 3D image;
d) calculate a matching score between the 2D digitally reconstructed radiography and the at least one 2D X-ray image;
e) calculate a registration score representative of a residual distance between data points of said candidate 3D shape and corresponding data points of the 3D image;
f) calculate an iteration score as a function of said registration score and said matching score, said function being referred to as iteration function;
g) determine whether the iteration score satisfies a predetermined exit criterion;
h) in response to determining that the predefined exit criterion is not satisfied, update the projection parameters of the digitally reconstructed radiography processing function and apply a set of deformation parameters to the candidate 3D shape, all computed based on the iteration score and on a gradient computed from said iteration function, and repeating steps (b)-(i), wherein the deformed 3D candidate shape is set as the candidate 3D shape; and
i) in response to determining that the exit criterion is satisfied, set the 3D model as the 3D candidate shape and outputting the 3D model and information indicative of the similarity transformation.

By similarity transform, it is meant a combination of a rigid transformation and an isotropic scaling function.

The device proposed herein thus allows reconstructing a 3D model of the exposed target anatomical structure of the patient, based on the predefined shape model and the at least one 3D image obtained intraoperatively from at least one 3D imaging sensor in a richer way as would be done preoperatively based on X-ray data only. In contrast with prior art solutions, the device proposed herein allows also for seamless intraoperative assistance of surgical planning or for helping towards the evaluation of the accuracy of the intervention.

Preferably, the registration score is point-to-plane error metric between the data points of the candidate 3D shape and the tangent plane at the corresponding data points in the 3D image. The registration score can also be a function of the square root of the average squared distances between data points of the candidate 3D shape and the corresponding data points in the 3D image.

Preferably, the 2D digitally reconstructed radiography is computed using a raytracing algorithm.

Preferably, the data points of the 3D image have been filtered to exclude data points representative of anatomical structures others than the target anatomical structure and/or data points relating to noise.

Preferably, determining whether the iteration score satisfies a predetermined exit criterion, comprises comparing the iteration score to a predefined threshold.

Preferably, the predefined exit criterion is configured to stop the iterations when, for a given number of iterations, changes in the iteration score are less than a given threshold value.

Preferably, the predefined shape model is a statistical shape model.

Preferably, the iteration score is a weighted function of the registration score and the matching score, the weights being configured to evolve during the iterations.

Preferably, the registration score and the matching score are calculated as weighted function, the weights being determined on the base of the confidence associated respectively to the data points of the 3D image and pixels in the 2D X-ray image.

Preferably, the matching score is calculated as a similarity function between the pixels of the 2D X-ray image and the pixels of the 2D digitally reconstructed radiography, said similarity function being chosen among: continuous Dice, pixel to pixel mean square distance, pixel-wise mean squared error, image features matching.

Preferably, the predefined shape model is generated based on demographic data, medical imaging data and/or diagnosis information of the patient.

Preferably, the predefined shape model associated to the target anatomical structure comprises a representation of at least one bone and, optionally at least one cartilage.

Another aspect of the invention pertains to a computer implemented method for reconstruction of a 3D model of an exposed target anatomical structure of a patient during surgery, said method comprising:

receiving:
- at least one 2D X-ray image comprising at least one portion of the target anatomical structure;
- at least one 3D image acquired from at least one 3D imaging sensor during surgery, wherein the at least one 3D image comprises data points representing at least one exposed portion of the target anatomical structure;
- a predefined shape model of the target anatomical structure;

a) setting a candidate 3D shape based on the predefined shape model;

b) computing a 2D digitally reconstructed radiography using a digitally reconstructed radiography processing function characterized by a set of projection parameters on the candidate 3D shape by;

c) registering at least part of the data points to a corresponding portion of said candidate 3D shape and compute a similarity transformation between the data points of said candidate 3D shape and corresponding data points of the 3D image;

d) calculating a matching score between the 2D digitally reconstructed radiography and the at least one 2D X-ray image;

e) calculating a registration score representative of a residual distance between data points of said candidate 3D shape and corresponding data points of the 3D image, by computing a rigid transformation between the candidate 3D shape and corresponding data points of the 3D image;

f) calculating an iteration score as a function of said registration score and said matching score, said function being referred to as iteration function;

g) determining whether the iteration score satisfies the predetermined exit criterion;

h) in response to determining that the exit criterion is not satisfied, updating the projection parameters of the digitally reconstructed radiography processing function and applying a set of deformation parameters to the 3D candidate shape, all computed based on the iteration score and on a gradient computed from said iteration function, and repeating steps (b)-(i), wherein the deformed 3D candidate shape is set as the candidate 3D shape; and i) in response to determining that the exit criterion is satisfied, setting the 3D model as the 3D candidate shape and outputting the 3D model and information indicative of the similarity transformation.

In addition, the disclosure relates to a computer program comprising software code adapted to perform a method for reconstruction of a 3D model of an exposed target anatomical structure compliant with any of the above execution modes when the program is executed by a processor.

The present disclosure further pertains to a non-transitory program storage device, readable by a computer, tangibly embodying a program of instructions executable by the computer to perform a method for reconstruction of a 3D model of an exposed target anatomical structure, compliant with the present disclosure.

Such a non-transitory program storage device can be, without limitation, an electronic, magnetic, optical, electromagnetic, infrared, or semiconductor device, or any suitable combination of the foregoing. It is to be appreciated that the following, while providing more specific examples, is merely an illustrative and not exhaustive listing as readily appreciated by one of ordinary skill in the art: a portable computer diskette, a hard disk, a ROM, an EPROM (Erasable Programmable ROM) or a Flash memory, a portable CD-ROM (Compact-Disc ROM).

Definitions

In the present invention, the following terms have the following meanings:

The terms "adapted" and "configured" are used in the present disclosure as broadly encompassing initial configuration, later adaptation or complementation of the present device, or any combination thereof alike, whether effected through material or software means (including firmware).

The term "processor" should not be construed to be restricted to hardware capable of executing software, and refers in a general way to a processing device, which can for example include a computer, a microprocessor, an integrated circuit, or a programmable logic device (PLD). The processor may also encompass one or more Graphics Processing Units (GPU), whether exploited for computer graphics and image processing or other functions. Additionally, the instructions and/or data enabling to perform associated and/or resulting functionalities may be stored on any processor-readable medium such as, e.g., an integrated circuit, a hard disk, a CD (Compact Disc), an optical disc such as a DVD (Digital Versatile Disc), a RAM (Random-Access Memory) or a ROM (Read-Only Memory). Instructions may be notably stored in hardware, software, firmware or in any combination thereof.

"Tridimensional (3D) model" refers to a three-dimensional digital (or virtual) model being a virtual object in 3 dimensions. The position and orientation of the model is known in the associated digital referential. The 3D model may be mathematically represented by a point cloud.

"Preoperative planning" in the context of surgery, refers to a list of actions to be performed during the different surgical phases. This surgical planning may be obtained by means of a simulation program carried out before the operation which uses a 3-dimensional digital model of the bone(s) of the patient that are the target of the surgery. In the case of a knee arthroplasty operation, for example, preoperative planning will consist of defining each of the cutting planes and drilling axes in relation to a three-dimensional model of the femur and tibia.

"(Data points) registration" refers to the process of transforming different sets of data points into one coordinate system. Image registration involves spatially transforming "moving" data points to align with "target" data points (i.e., image, model and the like). The reference frame (i.e.; referential) associated to the target data points is stationary, while the other datasets are transformed to match to the target.

ILLUSTRATIVE EMBODIMENTS

The present description illustrates the principles of the present disclosure. It will thus be appreciated that those skilled in the art will be able to devise various arrangements that, although not explicitly described or shown herein, embody the principles of the disclosure and are included within its scope.

All examples and conditional language recited herein are intended for educational purposes to aid the reader in understanding the principles of the disclosure and the concepts contributed by the inventor to furthering the art, and are to be construed as being without limitation to such specifically recited examples and conditions.

Moreover, all statements herein reciting principles, aspects, and embodiments of the disclosure, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

Thus, for example, it will be appreciated by those skilled in the art that the block diagrams presented herein may represent conceptual views of illustrative circuitry embodying the principles of the disclosure. Similarly, it will be appreciated that any flow charts, flow diagrams, and the like represent various processes which may be substantially represented in computer readable media and so executed by a computer or processor, whether or not such computer or processor is explicitly shown.

The functions of the various elements shown in the figures may be provided through the use of dedicated hardware as well as hardware capable of executing software in association with appropriate software. When provided by a processor, the functions may be provided by a single dedicated processor, a single shared processor, or a plurality of individual processors, some of which may be shared.

It should be understood that the elements shown in the figures may be implemented in various forms of hardware, software or combinations thereof. Preferably, these elements are implemented in a combination of hardware and software on one or more appropriately programmed general-purpose devices, which may include a processor, memory and input/output interfaces.

Figure 1:
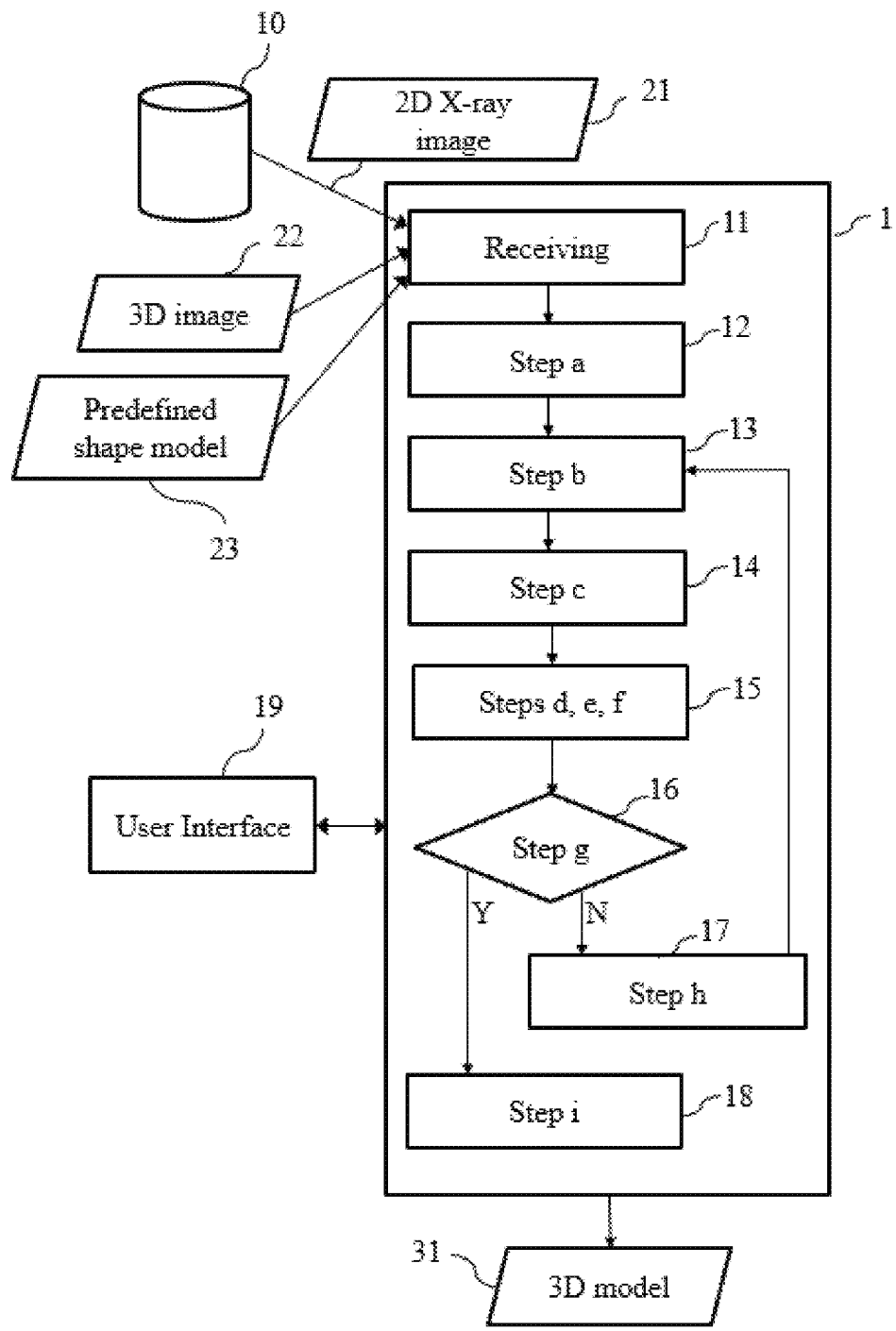
FIG. 1 is a block diagram representing schematically a particular mode of a device for reconstructing a 3D model compliant with the present disclosure.

The present disclosure will be described in reference to a particular functional embodiment of a device 1 for reconstruction of a 3D model 31 of an exposed target anatomical structure T of a patient during surgery, as illustrated on FIG. 1.

The device 1 is adapted to produce the 3D model 31 of the exposed target anatomical structure T and information indicative of the rigid transformation 32. This information, once obtained during the surgery, may be used to correctly reproduce the predefined surgical actions planned beforehand in the preoperative surgical planning.

Though the presently described device 1 is versatile and provided with several functions that can be carried out alternatively or in any cumulative way, other implementations within the scope of the present disclosure include devices having only parts of the present functionalities.

The device 1 is advantageously an apparatus, or a physical part of an apparatus, designed, configured and/or adapted for performing the mentioned functions and produce the mentioned effects or results. In alternative implementations, the device 1 is embodied as a set of apparatus or physical parts of apparatus, whether grouped in a same machine or in different, possibly remote, machines. The device 1 may e.g. have functions distributed over a cloud infrastructure and be available to users as a cloud-based service, or have remote functions accessible through an API.

In what follows, the modules are to be understood as functional entities rather than material, physically distinct, components. They can consequently be embodied either as grouped together in a same tangible and concrete component, or distributed into several such components. Also, each of these modules are possibly themselves shared between at least two physical components. In addition, the modules are implemented in hardware, software, firmware, or any mixed form thereof as well. They are preferably embodied within at least one processor of the device 1.

The device 1 comprises a module 11 for receiving the following input data: at least one 2D X-ray image 21, at least one 3D image 22 and a predefined shape model 23 of the target anatomical structure T. All these input data may be stored in one or more local or remote database(s) 10. The latter can take the form of storage resources available from any kind of appropriate storage means, which can be notably a RAM or an EEPROM (Electrically-Erasable Programmable Read-Only Memory) such as a Flash memory, possibly within an SSD (Solid-State Disk).

More in details, the 2D X-ray images 21 comprising at least one portion of the target anatomical structure T. In the exemplary case of a Total Knee Arthroplasty (TKA), the target anatomical structure T represented in the 2D X-ray images 21 is a femur or a tibia. More generally, the target anatomical structure T can be any bone structure. In a preferred embodiment at least two or three 2D X-ray images 21 are received as input in the module 11 to improve the quality of the 3D model 31 to produce. Said at least two or three 2D X-ray image are acquired from different angles, as known by the skilled person. Generally, acquisition of multiple 2D X-ray images 21 is included in the clinical routine for patient that will undergo TKA surgery.

The 3D image 22 received from the module 11 are acquired from at least one 3D imaging sensor during surgery. The at least one 3D image 22 comprises data points representing at least one exposed portion of the target anatomical structure T (e.g., femur or tibia).

The module 11 is configured to receive the 3D image 22, for example from a communication network, from the at least one 3D imaging sensor which is present in the surgical theater and positioned in such a way to comprise in its field of view at least a portion of the surgical field comprising the target anatomical structure T. During an orthopedic surgery, the surgeon proceeds to the exposure of the target anatomical structure T, which in this case may be a bone, on which surgical operations, such as for example, machining or drilling have to be performed. The surgical field, which is basically the region of the patient on which the surgery is to be performed, will comprise the exposed target anatomical structure T and the surrounding structures B such as tissues (i.e., cartilages, tendons, muscles, skin, or a bone which is not targeted during the surgery, and the like) and/or artificial structures (i.e., bone screw, surgical tools, grasping tools etc.).

The 3D imaging sensor refers to a sensor for acquiring topological data of a real scene in 3 dimensions. These topological data are recorded in the form of a point cloud, and/or a depth map. Herein after the term "data points" will be used to refer both to the point clouds or depth maps, as the person skilled in the art knows how to perform registration on both point clouds or depth maps. Therefore, at least one portion of the data points of one 3D image 22 represents at least one exposed portion of the target anatomical structure T of the patient. The other data points are generally associated to the structures surrounding the target anatomical structure T comprised in the field of view of the 3D imaging sensor.

Multiple acquisition techniques may be utilized to obtain these topological data for example techniques based on the measure of wave propagation time such as ultrasound or light (LIDAR, Time-of-Flight) or stereoscopic camera or sensor, which is a type of camera with two or more lenses with a separate image sensor or film frame for each lens. This allows the camera to simulate human binocular vision, and therefore gives it the ability to capture three-dimensional images. Other techniques may be based on light deformation, such as structured-light 3D scanners which project a pattern of light on an object and look at the deformation of the pattern on the object. The advantage of structured-light 3D scanners is speed and precision. Instead of scanning one point at a time, structured light scanners scan multiple points or the entire field of view at once. Scanning an entire field of view in a fraction of a second reduces or eliminates the problem of distortion from motion. Another class of techniques is based on laser scanning for sampling or scanning a surface using laser technology, such as hand-held laser or time-of-flight 3D laser scanner. More in general, any techniques known by the skilled artisan providing topological data of a real scene in 3 dimensions may be used for the implementation of the present invention.

The 3D image(s) 22 may be grayscale images, or colored depth (RGB-D) images among others. The 3D image(s) 22 may include numerical data, such as digital data. Those data may include individual image data in a compressed form, as well known to a person skilled in image compression, such as e.g., in compliance with e.g., in compliance with JPEG (for Joint Photographic Experts Group), JPEG 2000 or HEIF (for High Efficiency Image File Format) standard.

As the 3D image(s) 22 is (are) acquired by the 3D imaging sensor, the data points of the 3D images are associated to a sensor referential, notably the referential of the 3D imaging sensor.

For a given registration running, the 3D image(s) 22 may be derived from a unique 3D imaging sensor used to acquire at least one 3D image of at least a portion of the surgical field comprising the target anatomical structure T. Alternatively, the 3D image(s) 22 may be derived from two or more 3D imaging sensors, or even from two or more different kinds of 3D imaging sensors. In this case, data from multiple sensors could be combined into a single fused point cloud or depth map. Alternatively, the 3D point cloud could also be obtained via the digitization of the target anatomical structure's surface using a probe tracked by an optical tracking system.

The predefined shape model 23 may be the mean shape from a statistical shape model (SSM) that realistically describes the anatomy of the target anatomical structure T. The statistical shape model (SSM) also describes the variation of the anatomy of the target anatomical structure T in any population by conventional multivariate statistics of dense sets of homologous landmarks representing the shape of the underlying structures. Statistical shape modeling provides a powerful tool for describing the target T anatomy. By linearly combining the variance of the shape of a population of patients, statistical shape models (SSMs) identify its main modes of variation and may approximate the total variance of that population to a selected threshold, while reducing its dimensionality.

Figure 2:
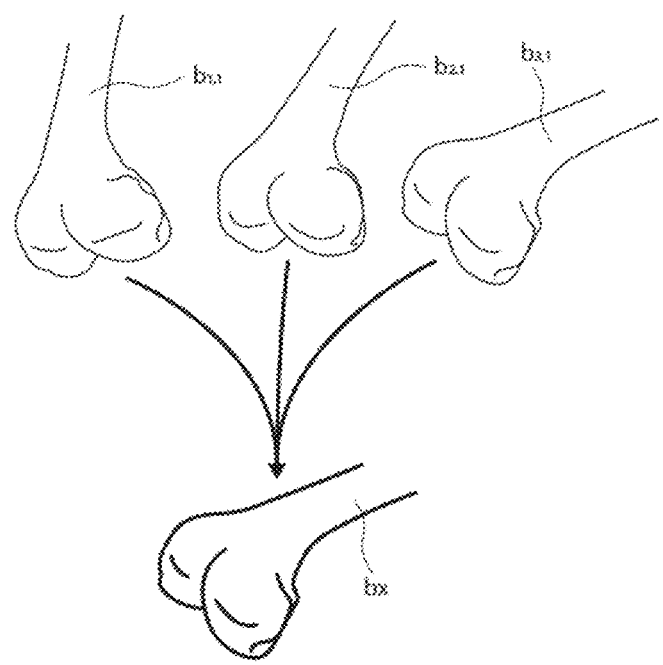
FIG. 2 is a schematic representation of how, according to one embodiment, the device constructs a database from different 3D files of target anatomical structures (e.g. bones) used to generate a statistical shape model.

The predefined shape model 23 may be retrieved from a database 10 or alternatively it may be calculated from a modeling module (not represented) part of the device 1. In one example, the predefined shape model 23 is generated based on demographic data and/or diagnosis information of the patient. The modeling module may be configured to access large database of 3D meshes of bones (i.e., including the target anatomical structure T) from patients, from a population representative of the target patients for the surgical procedure concerned. These 3D meshes of bones are coarsely aligned by the automatic placement of anatomical landmarks, enabling their rigid registration. A groupwise deformable registration algorithm may be then applied to these bones meshes, allowing a dense matching of surface points. A statistical model of the bone shape is obtained by performing a principal component analysis (PCA) on a densely sampled subset of points within the registered surfaces. This statistical model describes the morphologic features of the set of bone models from the input data, synthetically into a space of fundamental modes of variations. The calculation of the statistical shape model is schematically represented in FIG. 2, where the bone database can be expressed as a combination of a mean shape and of a set of parameters $b_{1,1}$, $b_{2,1}$, $b_{3,1}$ . . . representing principal modes of variation. A given bone mesh $b_x$. can be computed via a linear combination of the mean shape and these parameters. Other methods for the generation of a statistical shape model may be used by the modeling module as known by the person skilled in the art.

In one example, disregarding the method implemented to obtain it, the modeling module is configured to generate the predefined shape model 23 comprising a statistical shape model of a femur of the patient (i.e., target anatomical structure T) representing the totality of the bone surface or at least the portion of the bone surface on which the surgeon as to operate, notably the femur head and the distal part of the femur. In this example, the SSM module is configured to generate the predefined shape model 23 further comprising a statistical shape model of the femur representing the integrality of the bone surface of the distal or proximal epiphysis.

In one example the modeling module is configured to access a database of femurs and tibias 3D models, extracted from a series of segmented CT scans. The modeling module then jointly registers them to each other through a landmark matching algorithm after a first manual alignment. A statistical shape model is then built by sampling arbitrary landmarks uniformly on the registered surfaces and applying the inverse transformation of each shape to recover the position of each landmark in each original shape. The resulting model contains information of the mean shape and its variations with respect to the database. Principal Component Analysis (PCA) is then used on the bone database to find parameters modelling the shapes variations. For the statistical shape model to be representative of a given population, a large learning database of shapes including normal and pathologic shapes of subjects is used.

The device 1 may further comprise a module 12 configured to perform the step a of setting a candidate 3D shape based on the predefined shape model 23. The candidate 3D shape may be chosen as an average model among models from a large database of 3D meshes of bones (i.e., including the target anatomical structure T) from patients, from a population representative of the target patients for the surgical procedure concerned. More in details, the module 12 may be configured to perform an optional step of pre-processing of the 2D X-ray image(s) 21 configured to segment the contours of the bones represented in the 2D X-ray image(s) 21.

The device 1 also comprises a module 13 configured to perform the step b of computing a 2D digitally reconstructed radiography image using a digitally reconstructed radiography processing function on the candidate 3D shape. Examples of processing functions are raycasting, splatting and voxel projection algorithms, shear-warp factorization, or light fields algorithms. A segmentation step may be implemented on the 2D digitally reconstructed radiography image so as to extract the 2D contours of the target anatomical structure T. The 2D digitally reconstructed radiography may be computed using a raytracing algorithm.

A module 14 of the device 1 may be configured to perform the step c of registering a corresponding portion of said candidate 3D shape to at least part of the 3D image data points 22. This process yields an estimate of a rigid transformation that aligns the 3D image data points to the candidate 3D shape. The module 14 may be configured to perform a preprocessing step configured to filter the 3D image data points 22 so as to remove as much as possible data points associated to noise, artefacts or tissues that does not belong to the target anatomical structure T.

The device 1 further comprises a scoring module 15 configured to perform steps d, e, and f of calculating the matching score, the registration score and the iteration score. The scoring module 15 may calculate the matching score, between the 2D digitally reconstructed radiography model and the at least one 2D X-ray image 21, using different intensity-based similarity metrics such as normalized cross-correlation, entropy of difference, gradient correlation or gradient difference. The definition of such metrics is for example given in the article "*Comparison of similarity measures for rigid-body CT/Dual X-ray image registrations*", by Kim, Jinkoo, et al, Technology in cancer research & treatment 6.4 (2007): 337-345". Alternatively, the matching score may be calculated as pixel to pixel mean square distance, or a pixel-wise mean squared error. In one example, the matching score is calculated as weighted function, wherein the weights are determined on the base of the confidence associated to pixels in the 2D X-ray image 21. For instance, when the target anatomical structure T is a bone, pixels corresponding to the bone contours hold higher confidence.

As for the matching score, the scoring module 15 may calculate the registration score using different type of methods. In on example, the registration score is a point-to-plane error metric, corresponding to the minimization of the sum of the squared distances between the data points of the candidate 3D shape and the tangent plane at the corresponding data points in the 3D image. In another example, the registration score may be function of the square root of the average squared distances between data points of the candidate 3D shape for the current iteration and the corresponding data points in the 3D image 22. In one example, the registration score is calculated as a weighted function wherein the weights are determined on the base of the confidence associated to the data points of the 3D image 22. For instance, when the target anatomical structure T is a bone, points corresponding to the center of the bone hold higher confidence than for instance points corresponding to edges of the bone. Indeed, the resulting localization of the edges could be biased by soft tissues located on the edges. The order of calculation between matching score and the registration score may be inversed.

The scoring module 15 is then configured to calculate an iteration score as a function of said registration score and said matching score. This function is referred to as iteration function. The iteration score may be obtained as a linear combination, such a sum or a weighted sum, of the registration score and said matching score. In the case the iteration score is a weighted function of the registration score and the matching score, the weights are configured to be adapted during the iterations according to the variations of the current cost value or the total number of iterations, according to an optimization algorithm.

The device 1 further comprises a verification module 16 for determining whether the iteration score satisfies a predetermined exit criterion. The verification module 16 is configured to compare the iteration score to a predefined threshold. For instance, the predefined threshold is empirically determined via off-line tests, where models from known databases, or computed from cadaveric samples, are tested. In one example, the predefined exit criterion is configured to stop the iterations when, for a given number of iterations, the iteration score is unchanged.

The device 1 further comprises a deformation module 17 to perform the step h. Indeed module 17 is configured to, in response of the fact that module 16 has determined that the predefined exit criterion is not satisfied, deform the candidate 3D shape based on the calculated iteration score. More precisely, at step h, a set of deformation parameters are updated according to the variations of the iteration function via an optimization algorithm. The deformation parameters are the parameters found by the previously applied Principal Component Analysis (PCA) and which model the shapes variations. The deformation parameters are mathematical quantities. Then, module 17 sets the deformed 3D candidate shape as candidate 3D shape for a new iteration and therefore triggers instructions for repeating steps (b)-(i) (i.e., the new iteration).

The device 1 further comprises an exit module 18 to perform the step i. This module 18 is configured to set the 3D model 31 as the 3D candidate shape and outputting the 3D model 31 and information indicative of the rigid transformation 32, whenever the module 16 determines the exit criterion is satisfied.

The device 1 is interacting with a user interface 19, via which information can be entered and retrieved by a user. The user interface 19 includes any means appropriate for entering or retrieving data, information or instructions, notably visual, tactile and/or audio capacities that can encompass any or several of the following means as well known by a person skilled in the art: a screen, a keyboard, a trackball, a touchpad, a touchscreen, a loudspeaker, a voice recognition system.

Figure 3:
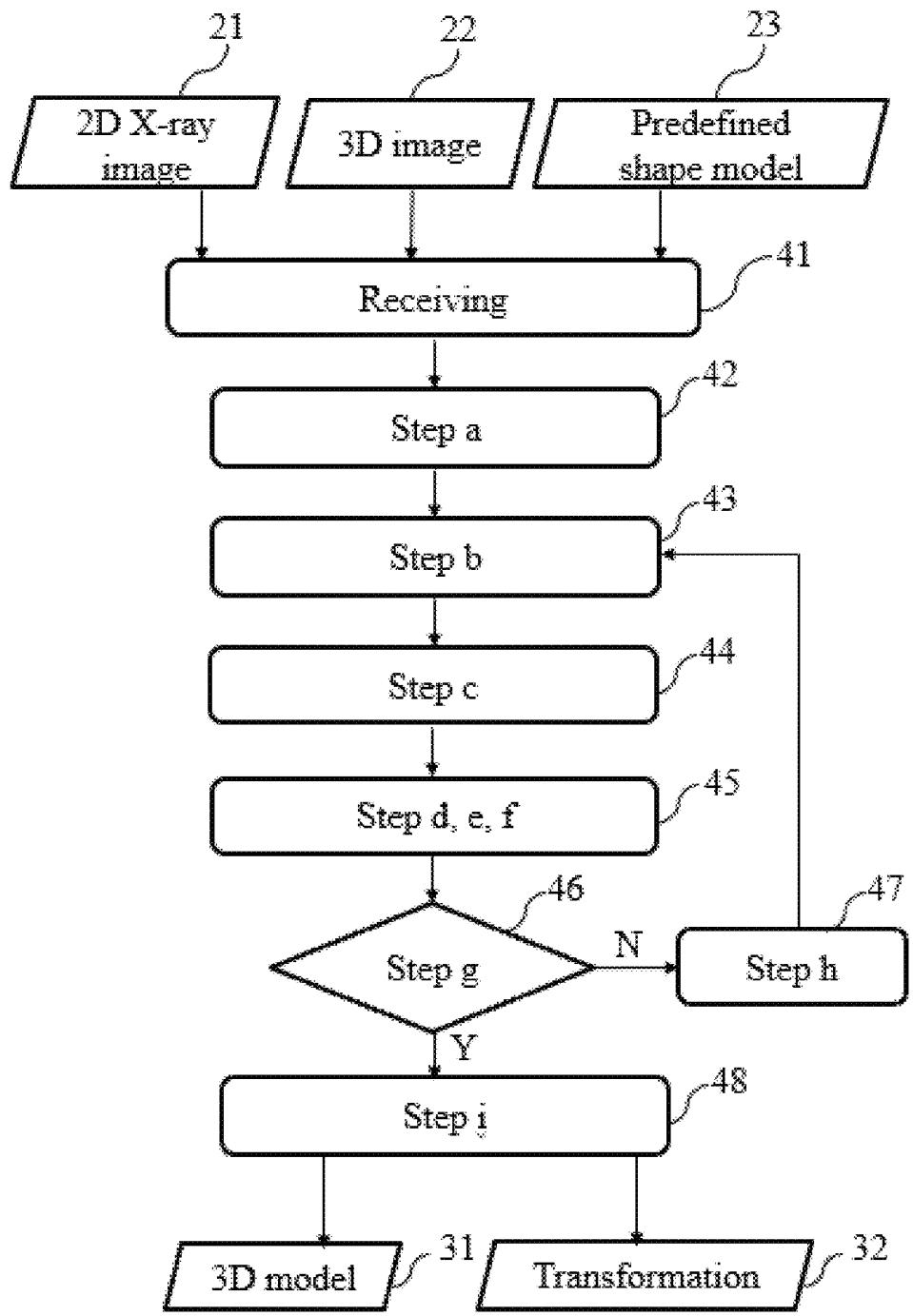
FIG. 3 is an example of a flow-chart representing a method for the reconstruction of a 3D model of an exposed target anatomical structure of a patient during surgery according to embodiments of the invention.

In its automatic actions, the device 1 may for example execute the following process illustrated on FIG. 3:
- receiving the at least one 2D X-ray image 21, the at least one 3D image 22 and the predefined shape model 23 (step 41),
- setting the candidate 3D shape based on the predefined shape model 23 (step 42),
- computing a 2D digitally reconstructed radiography model of the candidate 3D shape (step 43),
- register to a corresponding portion of said candidate 3D shape to at least part of the 3D image data points 22 (step 44),
- calculating the matching score, the registration score and the iteration score (step 45),
- determining whether the iteration score satisfies a predetermined exit criterion (step 46),
- in response to determining that the predefined exit criterion is not satisfied, deforming the candidate 3D shape based on the iteration score, and repeating steps (b)-(i), wherein the deformed 3D candidate shape is set as the candidate 3D shape (step 47),
- in response to determining that the exit criterion is satisfied, setting the 3D model 31 as the 3D candidate shape and outputting the 3D model 31 and information indicative of the rigid transformation (step 48).

Figure 4:
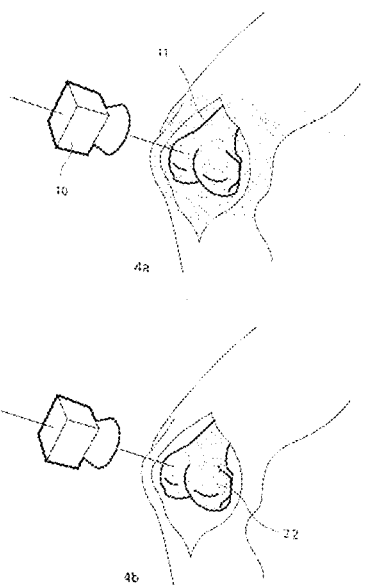
FIGS. 4a and 4b illustrate a process of capturing a 3D point cloud using a 3D imaging sensor.
Figure 4:

FIG. 4 illustrates a process of capturing a set of 3D data points 22 with a 3D imaging sensor. FIG. 4a shows a 3D imaging sensor 10 and a femur 11 of a patient. FIG. 4b shows a set of 3D image data points 22 captured by the 3D imaging sensor 10.

Figure 5:
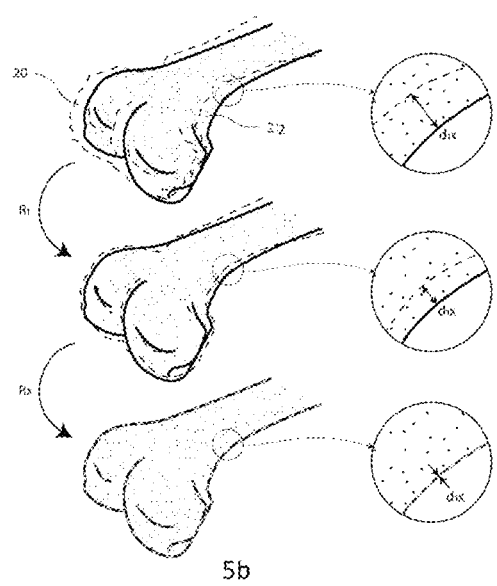
FIGS. 5a and 5b illustrate an iterative process of some of the steps of the flow-chart of FIG. 3.

FIG. 5a shows the predefined shape model at the first iteration superimposed to the set of 3D data points 22. FIG. 5b shows several iterations R1 of step h (or step 47) of deforming the candidate 3D shape based on the iteration score. The iteration R1 allows reducing distances such as a distance dix indicated on FIG. 5b between the current candidate 3D shape and the 3D image 22. FIG. 5b further shows a second iteration R2 successive to the first iteration R2, where the candidate 3D shape is once again deformed, so that the distance d1X is further reduced.

Figure 6:
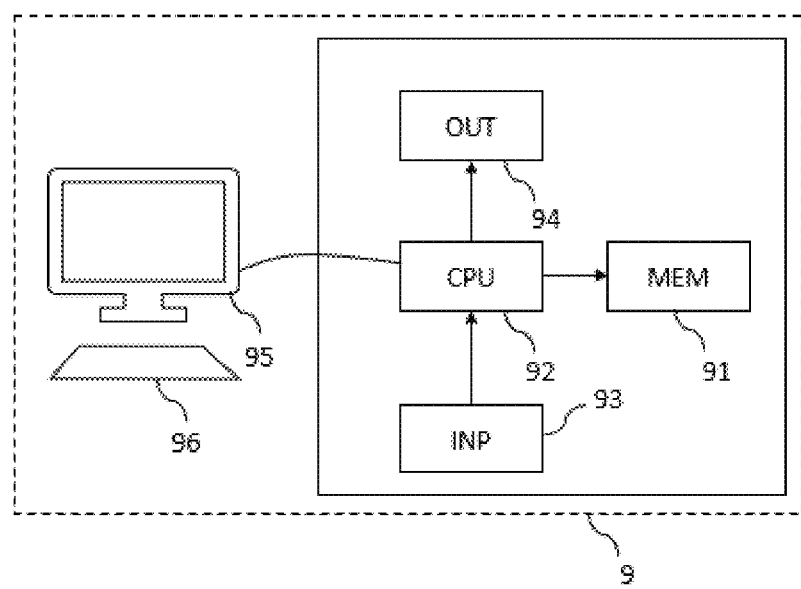
FIG. 6 illustrates an apparatus embodying a device for reconstructing a 3D model compliant with the present disclosure, such as the device of FIG. 1.

A particular apparatus 9, visible on FIG. 6, is embodying the device 1 described above. It corresponds for example to a workstation, a laptop, a tablet, a smartphone, or a head-mounted display (HMD).

The apparatus 9 comprises a memory 91 to store program instructions loadable into a circuit and adapted to cause a circuit 92 to carry out steps of the method of FIG. 4 when the program instructions are run by the circuit 92. The memory 91 may also store data and useful information for carrying steps of the present invention as described above.

The circuit 92 may be for instance:
- a processor or a processing unit adapted to interpret instructions in a computer language, the processor or the processing unit may comprise, may be associated with or be attached to a memory comprising the instructions, or
- the association of a processor/processing unit and a memory, the processor or the processing unit adapted to interpret instructions in a computer language, the memory comprising said instructions, or
- an electronic card wherein the steps of the invention are described within silicon, or
- a programmable electronic chip such as a FPGA chip (for «Field-Programmable Gate Array»).

The apparatus 9 may also comprise an input interface 93 for the reception of the at least one 2D X-ray image 21, the predefined shape model 23 and the 3D image 22, and an output interface 94 to provide the 3D model 31. The input interface 93 and the output interface 84 may together correspond to the user interface 19 of FIG. 1.

To ease the interaction with the computer, a screen 95 and a keyboard 96 may be provided and connected to the computer circuit 92.

The invention claimed is:

1. A device for reconstruction of a 3D model of an exposed target anatomical structure of a patient during surgery, said device comprising:
   - at least one input configured to receive:
     - at least one 2D X-ray image comprising at least one portion of the target anatomical structure;
     - at least one 3D image acquired from at least one 3D imaging sensor during surgery, wherein the at least one 3D image comprises data points representing at least one exposed portion of the target anatomical structure;
     - a predefined shape model of the target anatomical structure;
   - at least one processor configured to compute the 3D model of the exposed target anatomical structure via an iterative method following the steps below:
     a) set a candidate 3D shape based on the predefined shape model;
     b) compute a 2D digitally reconstructed radiography model using a digitally reconstructed radiography processing function characterized by a set of projection parameters on the candidate 3D shape;
c) register a corresponding portion of said candidate 3D shape to at least part of the 3D image data points and computing a similarity transformation between the data points of said candidate 3D shape and corresponding data points of the 3D image;
d) calculate a matching score between the 2D digitally reconstructed radiography model and the at least one 2D X-ray image;
e) calculate a registration score representative of a residual distance between data points of said candidate 3D shape and corresponding data points of the 3D image;
f) calculate an iteration score as a function of said registration score and said matching score, said function being referred to as iteration function:
g) determine whether the iteration score satisfies a predetermined exit criterion:
h) in response to determining that the predefined exit criterion is not satisfied, update the projection parameters of the digitally reconstructed radiography processing function and apply a set of deformation parameters to the candidate 3D shape, all computed based on the iteration score and on a gradient computed from said iteration function, and repeating steps (b)-(i), wherein the deformed 3D candidate shape is set as the candidate 3D shape; and
i) in response to determining that the exit criterion is satisfied, set the 3D model as the 3D candidate shape and outputting the 3D model and information indicative of the similarity transformation.

2. The device according to claim 1, wherein the registration score is a point-to-plane error metric between data points of the candidate 3D shape and a tangent plane at the corresponding data points in the 3D image.

3. The device according to claim 1, wherein the registration score is a function of the square root of the average squared distances between data points of the candidate 3D shape and the corresponding data points in the 3D image.

4. The device according to claim 1, wherein the 2D digitally reconstructed radiography is computed using a raytracing algorithm.

5. The device according to claim 1, wherein the data points of the 3D image have been filtered to exclude data points representative of anatomical structures others than the target anatomical structure and/or data points relating to noise.

6. The device according to claim 1, wherein, determining whether the iteration score satisfies a predetermined exit criterion, comprises comparing the iteration score to a predefined threshold.

7. The device according to claim 1, wherein the predefined exit criterion is configured to stop the iterations when, for a given number of iterations, changes in the iteration score are less than a given threshold value.

8. The device according to claim 1, wherein the predefined shape model is a statistical shape model.

9. The device according to claim 1, wherein the iteration score is a weighted function of the registration score and the matching score, the weights being configured to evolve during the iterations.

10. The device according to claim 1, wherein the registration score and the matching score are calculated as a weighted function, the weights being determined on the base of the confidence associated respectively to the data points of the 3D image and pixels in the 2D X-ray image.

11. The device according to claim 1, wherein the matching score is calculated as a similarity function between the pixels of the 2D X-ray image and the pixels of the 2D digitally reconstructed radiography, said similarity function being chosen among: continuous Dice, pixel to pixel mean square distance, pixel-wise mean squared error, image features matching.

12. The device according to claim 1, wherein the predefined shape model is generated based on demographic data, medical imaging data and/or diagnosis information of the patient.

13. The device according to claim 1, wherein the predefined shape model associated to the target anatomical structure comprises a representation of at least one bone and, optionally at least one cartilage.

14. A computer implemented method for reconstruction of a 3D model of an exposed target anatomical structure of a patient during surgery, said method comprising:
receiving:
at least one 2D X-ray image comprising at least one portion of the target anatomical structure;
at least one 3D image acquired from at least one 3D imaging sensor during surgery, wherein the at least one 3D image comprises data points representing at least one exposed portion of the target anatomical structure:
a predefined shape model of the target anatomical structure;
a) setting a candidate 3D shape based on the predefined shape model;
b) computing a 2D digitally reconstructed radiography using a digitally reconstructed radiography processing function characterized by a set of projection parameters on the candidate 3D shape;
c) registering a corresponding portion of said candidate 3D shape to at least part of the data points and computing a similarity transformation between the data points of said candidate 3D shape and corresponding data points of the 3D image;
d) calculating a matching score between the 2D digitally reconstructed radiography and the at least one 2D X-ray image;
e) calculating a registration score representative of a residual distance between data points of said candidate 3D shape and corresponding data points of the 3D image, by computing a rigid transformation between the candidate 3D shape and corresponding data points of the 3D image;
f) calculating an iteration score as a function of said registration score and said matching score, said function being referred to as iteration function;
g) determining whether the iteration score satisfies the predetermined exit criterion;
h) in response to determining that the exit criterion is not satisfied, updating the projection parameters of the digitally reconstructed radiography processing function and applying a set of deformation parameters to the 3D candidate shape, all computed based on the iteration score and on a gradient computed from said iteration function, and repeating steps (b)-(i), wherein the deformed 3D candidate shape is set as the candidate 3D shape; and
i) in response to determining that the exit criterion is satisfied, setting the 3D model as the 3D candidate shape and outputting the 3D model and information indicative of the similarity transformation.

15. A non-transitory computer-readable medium comprising instructions which, when executed by a computer, cause the computer to carry out the method of claim 14.

* * * * *